US00PP28289P3

(12) United States Plant Patent
Danziger

(10) Patent No.: US PP28,289 P3
(45) Date of Patent: Aug. 15, 2017

(54) ***PETUNIA* PLANT NAMED 'DCASAUTMYS'**

(50) Latin Name: *Petunia sensu wijsman*
Varietal Denomination: DCASAUTMYS

(71) Applicant: Gavriel Danziger, Mishmar Hashiva (IL)

(72) Inventor: Gavriel Danziger, Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 127 days.

(21) Appl. No.: 14/545,657

(22) Filed: Jun. 2, 2015

(65) Prior Publication Data

US 2016/0360686 P1 Dec. 8, 2016

(51) Int. Cl.
*A01H 5/02* (2006.01)

(52) U.S. Cl.
USPC ..... Plt./356.1

(58) Field of Classification Search
USPC ..... Plt./263.1, 356.1, 356.13
See application file for complete search history.

*Primary Examiner* — Susan McCormick Ewoldt
*Assistant Examiner* — Karen Redden
(74) *Attorney, Agent, or Firm* — Cassandra Bright

(57) ABSTRACT

A new and distinct *Petunia* cultivar named 'DCASAUTMYS' is disclosed, characterized by a mounded, ball-shaped growth habit, very well branched plant form, medium vigor and an abundance of large light yellow flowers with brown centers, maturing to beige with violet centers. The new variety is a *Petunia*, normally produced as an outdoor garden or container plant.

2 Drawing Sheets

Figure 1:
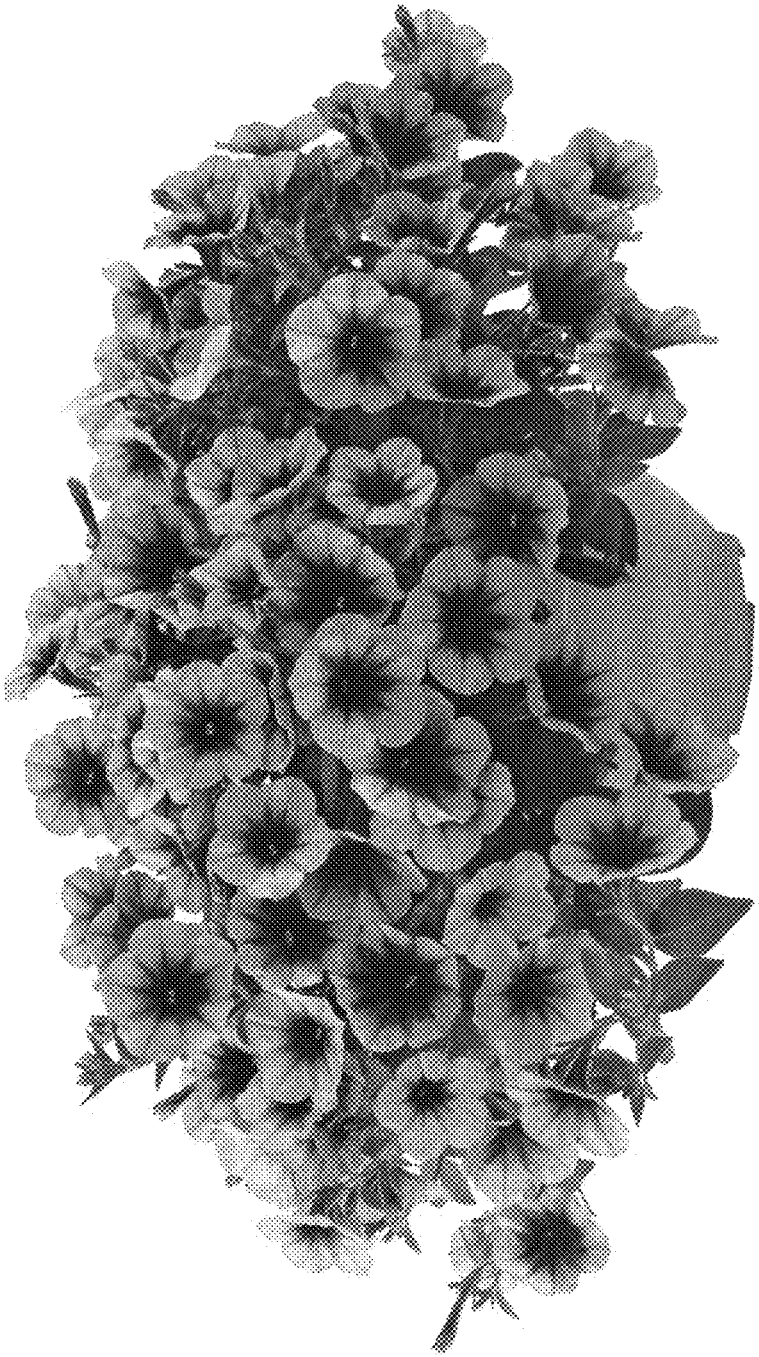

Latin name of the genus and species: *Petunia sensu wijsman.*

Variety denomination: 'DCASAUTMYS'.

BACKGROUND OF THE INVENTION

The new *Petunia* cultivar is a product of a planned breeding program conducted by the inventor, Gavriel Danziger, in Mishmar Hashiva, Israel. The objective of the breeding program was to produce new *Petunia* varieties for ornamental commercial applications. The cross resulting in this new variety was made during November of 2011.

The seed parent is the, unpatented, proprietary variety referred to as *Petunia 'cv.* 11-4698'. The pollen parent is the unpatented, propriety variety referred to as *Petunia 'cv.* 11-4527'. The new variety was discovered in May of 2012 by the inventor in a group of seedlings resulting from the 2011 crossing, in a research greenhouse in Mishmar Hashiva, Israel.

Asexual reproduction of the new cultivar was performed by terminal vegetative cuttings. This was first performed at a research greenhouse in Mishmar Hashiva, Israel in May of 2012 and has shown that the unique features of this cultivar are stable and reproduced true to type in more than 25 successive generations.

SUMMARY OF THE INVENTION

The cultivar 'DCASAUTMYS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCASAUTMYS' These characteristics in combination distinguish 'DCASAUTMYS' as a new and distinct *Petunia* cultivar:

1. Very branched plant with medium vigor.
2. Mounded, ball-shaped growth habit.
3. Large flower size.
4. Abundant flowering.
5. Flowers color is light yellow with a brown center, maturing to beige with a violet center.

Plants of the new cultivar 'DCASAUTMYS' are similar to plants of the seed parent in most horticultural characteristics, however, plants of the new cultivar 'DCASAUTMYS' differ in the following;

1. Mounded ball-shaped growth habit, whereas the seed parent has a semi-upright growth habit.
2. Smaller flower size than the seed parent.
3. Flowers color is light yellow with brown center, maturing to beige with violet center. The seed parent flowers are nearly black with yellow stripes.
4. More flowers than the seed parent.
5. Less plant vigor than the seed parent.

Plants of the new cultivar 'DCASAUTMYS' are similar to plants of the pollen parent in most horticultural characteristics, however, plants of the new cultivar 'DCASAUTMYS' differ in the following;

1. Mounded ball-shaped growth habit, whereas the pollen parent has a ball-shaped growth habit.
2. Larger flower size than the pollen parent.
3. Flowers color is light yellow with brown center, maturing to beige with violet center. The pollen parent has flowers which are pink with dark veins.
4. More flowers per plant than the pollen parent.
5. Larger plant with greater vigor than the pollen parent.

COMMERCIAL COMPARISON

Plants of the new cultivar 'DCASAUTMYS' are comparable to the patented commercial variety *Petunia* 'DANRAY1' U.S. Plant Pat. No. 20,974. The two *Petunia* varieties are similar in most horticultural characteristics; however, the new variety 'DCASAUTMYS' differs in the following:

1. Flower size of this comparator is larger than the flower of the new variety.
2. Comparator flower color is white, the new variety has a light yellow flower with a brown center, maturing to beige with a violet center.
3. Plants of the comparator variety are more vigorous than plants of the new variety.
4. Average branch length of the comparator is longer than branches of the new variety.

Plants of the new cultivar 'DCASAUTMYS' can also be compared to the unpatented commercial variety *Petunia* 'DANRAY3'. The two *Petunia* varieties are similar in most horticultural characteristics; however, the new variety 'DCASAUTMYS' differs in the following:

1. Flower size of this comparator is larger than the flower of the new variety.
2. Flower color is light purple with dark purple veins, while the new variety has a light yellow flower with a brown center, maturing to beige with a violet center.
3. Plants of the comparator variety are more vigorous than plants of the new variety.
4. Average branch length of the comparator is longer than branches of the new variety.

BRIEF DESCRIPTION OF THE PHOTOGRAPHS

The accompanying photograph in FIG. 1 illustrates in full color a typical plant of 'DCASAUTMYS' grown in a nursery, in a 13 cm pot. Age of the plant photographed is approximately 90 days from a rooted cutting.

Figure 2:
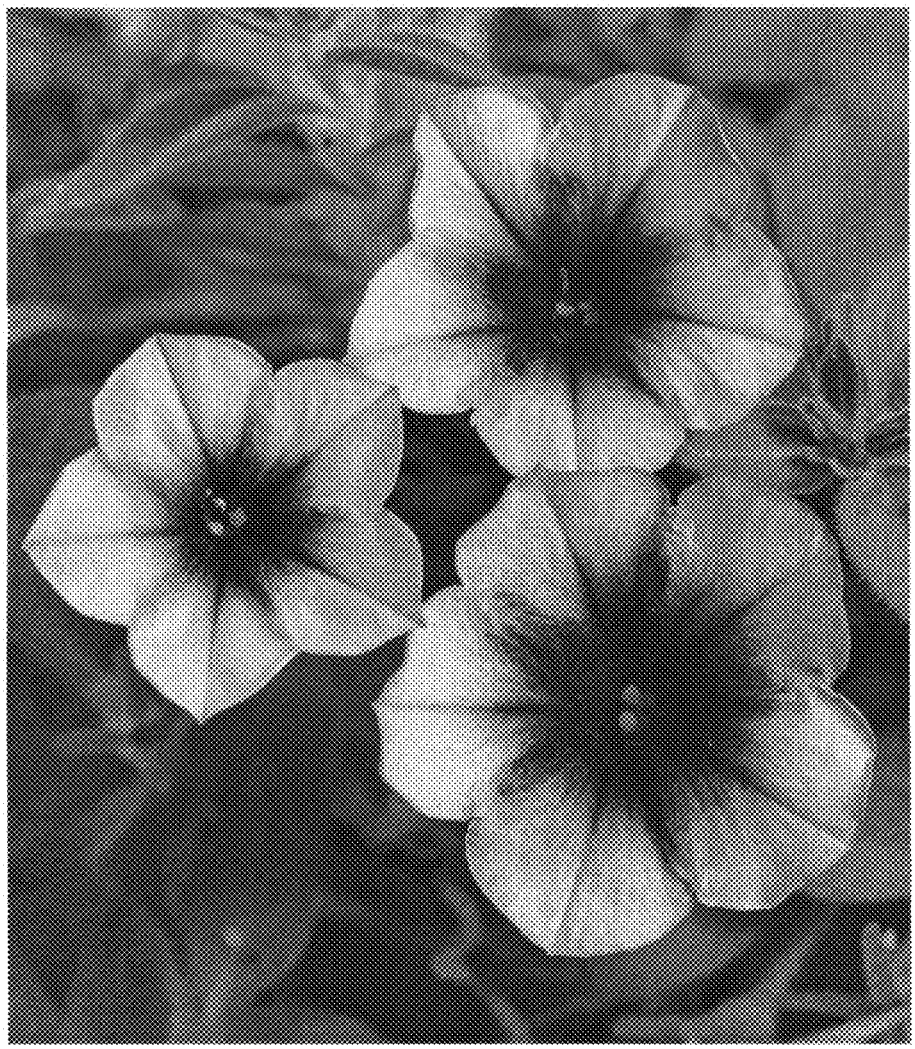

FIG. 2 illustrates a close up of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCASAUTMYS' plants grown outdoors and in greenhouse during the Spring, Summer and Autumn, in Mishmar Hashiva, Israel. The growing temperature ranged from 20° C. to 35° C. during the day and from 17° C. to 23° C. during the night. General light conditions are bright, normal sunlight. Measurements and numerical values represent averages of typical plant types.

Botanical classification: *Petunia* 'DCASAUTMYS'.

PROPAGATION

Type of propagation typically used: Vegetative terminal cutting.
Time to initiate roots: 10-14 days.
Root description: Fibrous.

PLANT

Age of plant described: Approximately 60 days from a rooted cutting.
Pot size of plant described: 13 cm.
Growth habit: Mounded.
Height: Approximately 20 cm.
Plant spread: About 55 cm.
Growth rate: Medium.
Branching characteristics: Very well branched.
Characteristics of primary lateral branches:
- *Quantity of primary lateral branches.*—8.
- *Length of primary lateral branches.*—About 28 cm.
- *Form.*—Cylindrical.
- *Diameter.*—About 0.4 cm.
- *Color.*—RHS Yellow-Green 144 A.
- *Texture.*—Pubescent.
- *Strength.*—Strong and flexible.

Internode length: 2 cm.

FOLIAGE

Leaf:
- *Arrangement.*—Opposite.
- *Quantity.*—Approximately 30 per branch.
- *Average length.*—6 cm.
- *Average width.*—3.5 cm.
- *Shape of blade.*—Ovate.
- *Apex.*—Acute.
- *Base.*—Tapered.
- *Margin.*—Entire.
- *Texture of top surface.*—Velvety.
- *Texture of lower surface.*—Velvety.
- *Color.*—Young foliage upper side: RHS Yellow-Green 146 A. Young foliage under side: RHS Yellow-Green 146 B. Mature foliage upper side: RHS Yellow-Green 146 A. Mature foliage under side: RHS Yellow-Green 146 B.
- *Venation.*—Type: Pinnate. Venation color upper side: RHS Yellow-Green 146 B. Venation color under side: RHS Yellow-Green 146 C.
- *Petiole.*—Length: 0.5 cm. Diameter: 0.3 cm. Color: RHS Yellow-Green 146 A. Texture: Velvety.

FLOWER

Natural flowering season: Spring, Summer, and Autumn in Mishmar Hashiva, Israel.
Days to flowering from rooted cutting: About 30 days.
Inflorescence and flower type and habit: Axillary, single flower, salverform shape, erect habit.
Rate of flower opening: 2 to 3 days from bud to fully opened flower.
Flower longevity on plant: 3-6 days.
Approximate quantity of flowers per plant: About 50.
Persistent or self-cleaning: Self-cleaning.
Bud:
- *Shape.*—Tubular.
- *Length.*—4.5 cm.
- *Diameter.*—About 1 cm.
- *Color.*—RHS Yellow-green 151 A.

Flower size:
- *Diameter.*—About 5.5cm.
- *Length.*—About 2.5 cm.
- *Flower tube diameter at distal end.*—About 1.0 cm.
- *Flower tube diameter at proximal end.*—About 0.4 cm.

Petals:
- *Length from throat.*—About 2.2 cm.
- *Width.*—About 2.5 cm.
- *Quantity.*—5.
- *Texture.*—Velvety.

*Apex*.—Blunt.
*Base*.—Fused.
*Margin*.—Entire.

Color:
*When opening*.—Upper surface: Overall appearance light yellow with brown center, Main color: RHS Yellow-Green 1 B. Center color: RHS Brown 200 B. Lower surface: RHS Yellow-Green 1 C.
*Fully opened*.—Upper surface: RHS Greyed-Yellow 160 B. Center color: RHS Greyed-Purple 187 A. Lower surface: RHS Greyed-Yellow 160 C. Flower throat (inside): RHS Greyed-Purple 187 A. Flower throat, vein: RHS Greyed-Purple 187 A. Flower tube (outside): RHS Greyed-Purple 187 B. Flower tube, vein: RHS Yellow-Green 151 B.
*Fading*.—Petals fading to: RHS Green-White 157B with Violet center, RHS Violet 83 B.

Calyx/sepals:
*Quantity per flower:* 5.
*Shape*.—Linear.
*Length*.—About 1.8 cm.
*Width*.—About 0.3 cm.
*Apex*.—Rounded.
*Base*.—Fused.
*Margin*.—Entire.
*Texture*.—Velvety.
*Color*.—Upper Surface: RHS Yellow-Green 146 A. Lower Surface: RHS Yellow-Green 146 B.

Peduncle: Not present.

Pedicel:
*Length*.—About 2 cm.
*Diameter*.—About 0.1 cm.
*Color*.—RHS Yellow-Green 146 B.
*Orientation*.—Straight, average angle of attachment 45 degrees.

Fragrance: None.

REPRODUCTIVE ORGANS

Stamens:
*Number (per flower)*.—5.
*Filament length*.—About 2 cm.

Anthers:
*Shape*.—Rounded.
*Length*.—About 0.1 cm.
*Color*.—RHS Yellow 5 B.

Pollen:
*Color*.—RHS Yellow 4 C.
*Amount*.—Abundant.

Pistils:
*Quantity per flower*.—1.
*Length*.—About 2.5 cm.
*Style*.—Length: about 1.8 cm. Color: RHS Yellow-green 149 B. Stigma: Shape: Rounded. Color: RHS Green 143 C. Ovary Color: RHS Green 143 A.

OTHER CHARACTERISTICS

Seeds and fruits: About 50 Black, rounded seeds of about 0.5 mm diameter, per one brown, conical capsule. Color values not accurately measured with the R.H.S. chart.

Disease/pest resistance: Neither resistance nor susceptibility to the normal diseases and pests of *Petunia* have been observed. Typical well known diseases include: *Botrytis cineria, Fusarium, Pythium, Phytophthora,* and *Rhizoctonia* species. Typical well known pests include: Leaf miners, spider mites, thrips and possibly caterpillars.

Temperature tolerance: Tolerates a range between 5° C. to 40° C.

What is claimed is:

1. A new and distinct cultivar of *Petunia* plant named 'DCASAUTMYS' as herein illustrated and described.

* * * * *